(12) United States Patent
Granier

(10) Patent No.: US 7,998,754 B2
(45) Date of Patent: Aug. 16, 2011

(54) IN VITRO METHOD FOR THE SIMULTANEOUS DETECTION AND IDENTIFICATION OF ANTIBIOTICS OF DIFFERENT CLASSES AND CORRESPONDING DIAGNOSTIC KIT

(75) Inventor: Benoit Granier, Rotheux-Rimiere (BE)

(73) Assignee: Unisensor S.A., Wandre (BE)

( * ) Notice: Subject to any disclaimer, the term of this patent is extended or adjusted under 35 U.S.C. 154(b) by 581 days.

(21) Appl. No.: 11/911,375

(22) PCT Filed: Apr. 13, 2006

(86) PCT No.: PCT/BE2006/000036
§ 371 (c)(1),
(2), (4) Date: Oct. 12, 2007

(87) PCT Pub. No.: WO2006/108248
PCT Pub. Date: Oct. 19, 2006

(65) Prior Publication Data
US 2008/0176342 A1    Jul. 24, 2008

(30) Foreign Application Priority Data

Apr. 14, 2005 (EP) ..................... 05447079

(51) Int. Cl.
*G01N 33/53* (2006.01)

(52) U.S. Cl. ........ 436/518; 436/514; 436/524; 436/525; 436/810; 435/287.1; 435/287.7; 422/425; 422/430

(58) Field of Classification Search ............. 436/514, 436/518, 524, 525, 810; 435/287.1, 287.7; 422/56, 57, 58, 61, 188
See application file for complete search history.

(56) References Cited

U.S. PATENT DOCUMENTS

| | | | |
|---|---|---|---|
| 5,434,053 | A | 7/1995 | Piasio |
| 6,319,466 | B1 * | 11/2001 | Markovsky et al. ............ 422/56 |
| 6,475,805 | B1 | 11/2002 | Charm et al. |
| 6,524,804 | B2 | 2/2003 | Degelaen et al. |
| 2005/0130152 | A1 * | 6/2005 | Granier et al. .................. 435/6 |

FOREIGN PATENT DOCUMENTS

| EP | 0 593 112 | 4/1994 |
|---|---|---|
| WO | WO 99/67416 A | 12/1999 |
| WO | WO 03/048770 A2 | 6/2003 |

OTHER PUBLICATIONS

Joris et al FEMS Microbiology Letters. vol. 70, No. 1. Jun. 15, 1990. pp. 107-113.*
Rowe, C. et al. (1999) "An array immunosensor for simultaneous detection of clinical analytes" Anal. Chem. 71:433-439.
Golemi-Kotra, D. et al. (2003) "Resistance to B-lactam antibiotics and its mediation by the sensor domain of the transmembrane blar signaling pathway in staphylococcus aureus" The Journal of Biological Chemistry, 278:18419-18425.
Verheijen, R. et al. (1998) "Development of a one step strip test for the detection of sulfadimidine residues" Analyst 123:2437-2441.
Hisao Oka, Chemical Analysis for Antibiotics Used in Agriculture, by AOAC International, 1995, ISBN 0-935584-57-9.
Kachab et al., "The development of an enzyme-linked immunosorbent assay (ELISA) for cephalexin." Journal of Immunology Methods, J Immunol Methods, 147(1):33-41, (1992).
Developing Immunochromatographic Test Strips: A Short Guide, Millipore, Lit. No. TB500 Printed in USA Nov. 1996, 96-204 SAME AS 01, © 2002, 2006.
Frens, G., "Controlled nucleation for the regulation of the particle size in mondisperse gold suspension" Nature (London), Phys. Sci., 241:20-22 (1973).
Dixon-Holland et al. "Competitive direct enzyme-linked immunosorbent assay for detection of sulfamethazine residues in swine urine and muscle tissue" J. Assoc. Off. Anal. Chem. 71:(6), pp. 1137-1140 (1988).

* cited by examiner

*Primary Examiner* — Bao Thuy L Nguyen
(74) *Attorney, Agent, or Firm* — Knobbe, Martens, Olson & Bear LLP

(57) ABSTRACT

The invention concerns a diagnostic kit for simultaneous assay of antibiotics of different classes. The kit contains a single reaction mixture containing at least one first labelled receptor, specific of recognition of β-lactams, a second labelled receptor, specifically and competitively identifying a tetracycline and a biotinylated nucleic acid fragment, an anti-sulfamide antibody and a labelled sulfamide analogue; and a recovery system in the form of a solid support comprising a nitrocellulose membrane whereon are fixed in three separate testing zones, respectively an antibiotic with β-lactam nucleus, an avidin and an antibody capable of specifically identifying the antisulfamide antibody, so that the labelling intensity detected on the recovery system at the three testing zones results independently from a competitive recognition of each antibiotic by its labelled receptor.

19 Claims, 1 Drawing Sheet

IN VITRO METHOD FOR THE SIMULTANEOUS DETECTION AND IDENTIFICATION OF ANTIBIOTICS OF DIFFERENT CLASSES AND CORRESPONDING DIAGNOSTIC KIT

RELATED APPLICATIONS

This application is a U.S. National Phase of international Application No. PCT/BE2006/000036, filed Apr. 13, 2006, designating the U.S. and published in French on Oct. 19, 2006 as WO 2006/108248, which claims the benefit of European Application No. 05447079.4, filed Apr. 14, 2005.

FIELD OF THE INVENTION

The present invention relates to a method for causing a collection of various biological recognition molecules that are specifically capable of detecting several distinct analytes with high sensitivity to simultaneously react in a single reaction mix and to determine the class of analytes to which each of the detected compounds belongs, provided that the principle of specific recognition of a given class of analytes cannot interfere with the principle of specific recognition of another class of analytes.

The invention also relates to the diagnostic kit specially designed for implementing the method.

TECHNOLOGICAL BACKGROUND

A fundamental principle that governs good practice of monitoring and checking the food chain requires to perform check analyses as far upstream as possible from production in order to be able to identify and isolate as quickly as possible the foodstuffs suspected of being contaminated.

As a general rule, when detecting tests, often called "screening" tests, are performed, a sample that was detected positive during a first check analysis is in fact only assumed to be actually positive and it will have to be subjected to a second test called "confirmation" test. On the other hand, if an initial screening test gives a negative result, this is sufficient and no further analysis needs to confirm the result[1] again.

One first consequence of this rule is that the first screening method must be able to handle the detection of a maximum number of compounds. The detecting or screening tests should thus preferably and logically be "multi-analyte tests."

A second consequence of this rule is that it is important to know the class to which belongs the compound discovered in a positive sample during the screening test so as to be able to directly switch to the confirmation method which is normally very specific since it is recommended that the compound concerned be isolated and identified.

A third consequence of this rule is that a screening test cannot give results of a "false negative" type since these will then elude analysis at this preliminary stage and will not be confirmed later.

Various methods for the detection of antibiotics are currently known:
  microbiological tests that measure the inhibitive power of a sample on the growth of a bacterial strain. This type of test requires a relatively long incubation period (between 3 and 16 hours) before the result is obtained. In general, these tests (Delvotest® SP, BRT Test, Copan™, Eclipse™, Valio™) can simultaneously recognize several classes of antibiotics since the bacterial strains used are often sensitive to several compounds of different classes. However, this type of test does not allow to identify the precise class to which the antibiotic compound tested belongs;
  for the detection of small molecules, in vitro tests work according to the principle of the competition between the compound sought that is present in the sample and a marked competitor that was deliberately introduced into the sample for a single recognition site that may either be a receptor or an antibody. In a formulation of the type ELISA (Enzyme Linked Immuno Sorbent Assay) or RIA (Radio Immuno Assay)/RRA (Radio Receptor Assay), the time required for an analysis is of the order of 2 to 6 hours. Some of these methods, in particular the RRA laboratory methods, allow the simultaneous detection of several compounds of different classes. In this case however, the method does not allow to identify the class to which the compound that gave the positive result belongs;
  the more complex physico-chemical methods that allow to isolate and identify the compound sought have until recently been mainly methods where a system of chromatographic separation is combined with a mass spectrometry detection system (GC/MS or LC/MS). These methods require to adapt particular procedures for each distinct compound to be identified. Sometimes a single compound or some of the compounds of a same class may be simultaneously analysed, sometimes all the compounds of a same class may be detected but this is never possible with compounds of different classes. In fact, the principle of chromatographic separation is characteristic of the physico-chemical properties of a given compound, these properties often being different from one class to another. In the case where the operator does not know the type of compound to be identified, he must consider as many methods as there are classes of compounds.

In recent years, much quicker methods have been developed. These methods, called "RAPID TESTS", are used to perform rapid screening tests on a large number of samples. In general, these methods use the recognition of the compounds sought in relation to a biological molecule according to the competition principle. To make the analysis quick and easy, these types of test work with membranous devices with lateral flow (Tetrasensor™, SNAP®, Beta-STAR™, ROSA). These tests are classified according to various classes of antibiotics but none of the products known to date allow to detect compounds belonging to different classes in a single operation.

Even if it is reasonable to envisage and to impose on the agri-food sector primary screening analyses, the sector involved will demand the most complete analysis possible that would preferably identify a maximum number of suspect compounds. It is indeed more practical and economical to perform a single multiple test from a single sample rather than to have to perform a specific test for each specific compound. This practice requires a great deal of time, sample management and cost. It acts as a brake upon good management and effective control of foodstuffs.

At this stage, checking effectiveness is thus greatly restricted by the lack of multi-analyte tests that would allow to detect all of the compounds of several classes of analytes in a single operation and in less than 10 minutes, for example.

In particular, the agri-food industry would be interested in a new method allowing to analyse compounds belonging to at least two different classes of antibiotics in a single operation.

The type of antibiotic that may be administered to animals may vary depending on whether the application is therapeutic or prophylactic, on the animal species, on the germ to fight against, on the veterinary practice, on the legislation in force, on the available means or even on the geographical region. In the case of some specific treatments, a mixture of medication is used. As a general rule, the practitioner uses antibiotic products selected from among all the commercially available compounds as he assesses which are most effective.

The main classes of antibacterial agents and antibiotics used are: penicillins and cephalosporines, tetracyclines, sulfamides, aminoglycosides and aminocyclitols, macrolides, chloramphenicols or other peptides, ionophores, nitrofuranes, quinolones, carbadox, etc. All these classes cover a very wide range of chemically different compounds.

It is thought that the sometimes intensive use of antibiotics in veterinary medicine and in agricultural production may have caused the emergence of bacterial strains that have become resistant to antibiotics. In order to safeguard human health and to legislate in this field, many countries (European Union, USA, Canada, etc.) have set maximum authorized limits for the residues (MRLs—maximum residue level) of antibiotics in foodstuffs[2]. To some extent these MRLs set the boundary between a positive sample and a negative one, i.e. between a rejected sample and an accepted sample.

In parallel, the Commission Decision of Aug. 12, 2002 established the minimum required performance limits (MRPLs) applicable to analytical methods to be used for examining samples and defined common criteria for the interpretation of results[3].

It is understood that the only analysis techniques for which it can be demonstrated, on the basis of verifiable proofs, that they are validated and have an error rate conforming to standard of less than 5% for the level considered, may be used for the purposes of screening in compliance with Directive 96/23/EC.

In 1995, an average of one percent of all samples analysed for their antibiotic content had a level higher than the MRL and gave a positive result. When these positive results were confirmed, the products most frequently involved were penicillins and tetracyclines[4].

STATE OF THE ART

A system for recognising tetracycline molecules is described in the Applicant's patent application WO-A-03/048770 entitled "Method for performing in vitro diagnosis using gene regulation mechanisms and corresponding diagnostic kit". This method does not allow to detect anything other than tetracyclines. In a preferred formulation, the reagents comprise a tetR receptor, isolated from the *E. Coli* genetic control mechanism, for the resistance to tetracyclines, an antibody capable of recognising the receptor and a protein A preparation conjugated with particles of colloidal gold. In addition, the recovery system is a specific and biotinylated fragment of DNA that can be fixed on a molecule of avidine attached to a nitrocellulose membrane. It is during incubation in the presence of the sample that the receptor and the fragment of DNA interact only in the absence of tetracycline. In this case, the fragment of DNA forms a complex with the receptor and a signal generated by the gold particles attached to the receptor appears. Otherwise, the receptor that has already recognized a tetracycline molecule is no longer capable of binding to the fragment of DNA and as a result no signal appears.

A system for recognising β-lactames is described in patent WO-A-99/67416 entitled "Method for determining antibiotics with β-lactame core in a biological liquid." According to this method, it is not possible to detect anything other than β-lactames. In a preferred formulation, the inventors describe on the one hand an isolated receptor of *Bacillus licheniformis*, purified and chemically bonded to biotin molecules, to which is associated an anti-biotin antibody preparation conjugated with particles of colloidal gold, and on the other hand a conjugate formed of a cephalosporine linked to a human immunoglobulin and fixed to a nitrocellulose membrane. In the case where the sample does not comprise β-lactame, the receptor attaches to the fixed antibiotic and a signal generated by the gold particles attached to the biotin receptor by means of an anti-biotin antibody attached to the gold is detected. Otherwise, if the receptor is inhibited during prior incubation with the sample to be tested, it is no longer capable of bonding with the fixed antibiotic, and as a result no signal appears.

A system of rapid sulfamide recognition is also known as described by R. Verheijen et al.[5] and entitled "Development of a one-step strip test for the detection of sulfadimidine residues". This system uses a principle similar to that of the above-mentioned detection of β-lactames. For one thing, an antibody specific to sulfadimidines is conjugated with particles of colloidal gold and it is a sulfadimidine that is conjugated with ovalbumin and fixed to a nitrocellulose membrane. If the sample comprises any sulfadimidines recognized by the antibody, it forms a complex that is incapable of subsequently finding the fixed compound and as a result will not be able to attach to it. Otherwise, in the absence of sulfadimidine in the sample, the conjugated antibody will be able to recognize the fixed sulfadimidine and a coloured signal will be appear. This article does not indicate the specificity of this test.

All the rapid methods and processes with lateral flow known to date only apply to the detection of a single class of compounds and to date there is no method for detecting in a single operation all the compounds belonging to at least two different classes of antibiotics. The main reasons for this are the technical incompatibility of bringing together independently and without interference all the agents required for the detection of each of the classes in a single process. The second difficulty lies in the way of achieving the identification of the class to which the compound detected belongs.

To summarize, the known rapid systems for the detection of small molecules (MW<2,000) work according to the principle of competition that requires the use of two particular elements which are, for one thing, a molecule that can specifically recognize the compound to be detected, this molecule generally being a bacterial receptor or an immunoglobulin (antibody) and for another, a competitor for the recognition site. Depending on the method chosen, one of the elements is fixed to a support and the other element is marked. In some cases (format 1, see below), it is the recognition molecule that is marked and an analogue of the analyte that is fixed; in other cases (format 2, see below), it is an analogue of the analyte that is marked and it is the recognition molecule that is attached to an insoluble fraction.

The originality of the tetracycline detection system lies in the fact that the receptor comprises two interdependent recognition sites and as a result, the competitor is not an analogue of the analyte sought but a fragment of DNA capable of binding to the second recognition site of the same receptor.

In all methods called "RAPID TEST", the assessment is made by comparing the intensity of the signal obtained in the "test" zone, i.e. at the point where the recovery element of the active receptor is fixed, with the intensity of another signal that is obtained in the "control" zone, i.e. at the point where other reagents (or the excess of reagents) are recovered. In general, when the intensity in the "test" zone is more marked than that in the "control" zone, the result is negative for the element sought.

In all the cases relating to the measurement of the β-lactame molecules, the recognition molecule is obtained from the *Bacillus* preparation and in every case, this molecule is marked after purification. To achieve this marking, the surface must undergo chemical modification. For example, it may be chemically attached to an enzyme, as is the case with the *Bacillus Stearothermophillus* receptor attached to peroxydase (EP-A-0 593 112 and U.S. Pat. No. 5,434,053 by Giest Brocades) or to a biotin, as is the case with the *Bacillus licheniformis* receptor attached to a biotin (WO-A-99/67416 and U.S. Pat. No. 6,524,804 by U.C.B. S.A.) or even with the *Bacillus Stearothermophillus* receptor directly conjugated with colloidal gold (U.S. Pat. No. 6,475,805 by Charm Inc.). With the exception of the Tetrasensor™ method, it is necessary to chemically modify the recognition molecule to obtain a coloured complex from it in the other cases known to date. As a result, it is necessary to purify it and to modify some of its surface substituents with the risk of modifying a major functionality or stability property.

In the other cases known to date, it is therefore generally impossible to work either with unpurified raw extracts or with receptors that would not be chemically modified.

In addition, the type of marking used in the measurement of the "tetracycline" is not compatible with the measurement of the β-lactames since, it entails that it is an immunoglobulin that is fixed to the "control" zone in all reported cases. In the case of document WO-99/67416, it is also an immunoglobulin that acts as the anchoring protein in order to fix the competitor to the "test" zone. The use of the protein A as in the measurement of tetracyclines, would inevitably cause a non-specific marking on one or both capture lines required for the detection of β-lactames.

In another approach, where it is necessary to resort to the use of the avidine-biotin combination in order to facilitate the fixing to the support or the marking, the avidine-biotin combination may only be used in a given method for a single specific recognition. Indeed, if an avidine forms an anchoring point, it will be possible for all biotinylated molecules to attach themselves there. In such a case, it is in particular not possible to envisage a test for the common detection of β-lactames and of tetracyclines that would be based for example on the combination of the two measurement principles described in document WO-A-99/67416 and in document WO-A-03/048770. In fact, in the first case, the receptor is biotinylated and then marked by means of anti-biotin-gold and in the second case, avidine is fixed to recover a biotinylated fragment of DNA. The combination of these two principles would then lead to a further conflict between the two independent systems using the avidine-biotin combinations. In a combination of the two existing systems, the biotinylated receptor of the β-lactame system would bind to the avidine required for recovering the DNA of the tetracycline system and as a result would cause a non-specific marking independently of the level of tetracycline in the sample. Moreover, the presence of antibiotin-gold in the mobile phase would interfere with the biotinylated DNA preventing it from finding the avidine required for its capture, which would lead to yet another conflict.

In a third approach, the combination of two independent recognition systems would require a quite complex system for reading and interpreting the result where each of the markers has to be assessed by its intensity relative to an internal reference. There would therefore be two "test" bands ("beta" and "tetra") and two "control" bands. This concept makes the analysis neither simple nor practical. In the context of the combination of the two tests, it would be better to assess the intensity of each test by comparison with each other. In such a procedure, the "test" zone for analyte no. 1 would become the "control" zone for analyte no. 2 and vice versa. In the case where the two classes of analytes concerned were present at the same time in a same sample, this approach would create no or almost no signal. This is rarely the case but if it occurred, the addition of a single reference is recommended in the form of a single control line that allows to assess more easily the relative intensity of both test signals in order to avoid difficulties of interpretation in the case of double contamination by β-lactames and tetracyclines. Obviously, this single control line would become necessary in the case where more than two tests were combined into a single method.

In a fourth approach, the materials chosen expressly and preferentially to form the dipstick device of the diagnostic kit must be compatible for the simultaneous analysis of the two classes of analytes. Indeed, in a preferred embodiment described in WO 99/67416, the use of the "Leukosorb®" membrane is recommended but it is not compatible with the approach that we recommend for the tetracycline test and would not be suitable for the multi-analyte measurement. Indeed, very strangely, in a formulation where both receptors are marked by their respective antibodies, it is impossible to obtain a clean cut-off point by the addition of β-lactames when the reagents meet the Leukosorb® membrane before they reach the capture point. This membrane, whose efficiency was demonstrated for the purification of milk and for the use in lateral flow, is the cause of non-specific recognition signals when the marking is achieved by means of antibodies and protein A conjugated with colloidal gold.

In a fifth approach, the choice of receptors involved in the recognition of all the compounds of each of the classes is important. This choice is not only determined by the recognition performance of the compounds but also by criteria of stability, structure, antigen reactivity, amino acid composition, etc.

As a conclusion, based on known methods, it is a priori impossible to bring together in a single method at least two independent methods, for example for the recognition by receptors to β-lactames and tetracyclines, without envisaging major modifications allowing to combine the required elements whilst ensuring that the system for recognising a compound does not interfere with the system for recognising another compound.

AIMS OF THE INVENTION

The present invention aims to provide a new diagnosis method allowing to simultaneously detect a (theoretically unlimited) combination of compounds that may belong to at least two distinct classes of analytes and to identify the class to which a detected compound actually belongs.

In particular, the invention aims to demonstrate the technical and practical feasibility of combining in a single method at least two detection mechanisms without interference between the working of one of them and the working of the other mechanism.

An additional aim of the invention is to demonstrate the technical feasibility of multi-analyte measurement that can rapidly be achieved, for example in less than 30 minutes and in a single analysis stage by means of a single sample.

An additional aim of the invention is to provide a method and an in vitro diagnostic kit for the simultaneous detection and measurement of at least two classes of analytes.

MAIN CHARACTERISTIC ELEMENTS OF THE INVENTION

A first aim of the present invention, as in the respective claims 1, 3, 4 and 10, relates to a diagnostic kit for the simultaneous and specific detection or quantification of at least two analytes belonging to different classes of antibiotics, namely at least two classes from the β-lactames, tetracyclines and sulfamides, characterized in that it generally comprises, for example:

for one thing, a single reactive mixture, preferably in the form of a solution or a lyophilisate, comprising at least two different biological molecules, each one capable of recognising, respectively, simultaneously and specifically, a determined analyte present in a sample that may comprise analytes belonging to said different classes of analytes;

and for another thing, a recovery system in the form of a single solid support to which are attached, in distinct known spatial positions, the respective ligands that are capable of specifically, selectively and exclusively recovering each one of said biological molecules comprised in said reactive mixture so as to identify by the position of the recovery on said support the type of class to which each of the analytes present in the sample belongs.

Depending on the case, either the fixed recovery element is a competitor analogue to the substance sought and the receptor in solution is marked or the competitor analogue in solution is marked and the fixed recovery element is the receptor. Mixed systems may also coexist according to the invention.

Preferred embodiments of the invention are described in secondary claims 2, 5 and 9 and 11-12.

A second aim of the invention, as in Claim 13, relates to a method for implementing a diagnostic kit according to any one of Claims 1 to 12, characterized by the following stages:

the above-mentioned reactive mixture is brought into contact with a sample to be identified in order to obtain a solution that is left to incubate at a temperature between 30° C. and 50° C. for 3 to 15 minutes;

a dipstick bearing the above-mentioned recovery system is immersed in the solution obtained and left to incubate for 3 to 15 minutes;

the result on the dipstick is interpreted either visually by the naked eye or by means of an optical dipstick reader.

In the preferred embodiments of the present invention, it is recommended to avoid for one thing purification and for another thing chemical modification of the receptor for example by using anti-receptor antibodies that are marked either directly with colloidal gold or preferably with protein A attached to colloidal gold. On the other hand, in the concept of multiple detection, the protein A marked with colloidal gold would act as a generic marker for all antibodies introduced into the solution.

In order to preserve the maximum functionality of the receptors and antibodies used in the present invention, one principle adopted is that no marking by chemical modification occurs. As a result, the present invention uses bacterial receptors in their most natural state possible. These receptors are marked by means of antibodies that will themselves be identified by a protein A conjugated with colloidal gold. In such a case, it is therefore exclusively the marking protein that will be attached to the gold and not the sensitive molecules for the recognition of the analytes concerned.

In this approach, all functional groups of sensitive recognition molecules are thus preserved. This advantage is exploited to the full when the goal is to exploit the activity of the receptors whose recognition mechanism depends on certain lateral chains such as lysine residues, for example. It is all the more important that, when a chemical modification occurs, in most cases reported, the modification involves $NH_3^+$ residues of the lateral lysine chains. As a conclusion, chemical attachment to lysines can cause deterioration of the lysines of the active site and thereby make the preparation partially inactive.

Marking by means of antibodies has the flexibility of non-fixed marking. In fact, chemical marking implies an irreversible covalent bond whereas the attachment of antibodies is reversible and subject to an equilibrium that may be shifted depending on the forces acting on it. Another advantage is to be able to adjust the marking stage in a second step. In fact, in a second formulation of the present invention, it is after the phase of recognition of the analyte by the receptor, whether the free analyte of the sample or the fixed analyte for the recovery, that the antibody recognizes the receptor.

For various reasons of costs or stability, but also for perfect integration into a multi-analyte test, the present invention recommends the preferred use of a β-lactame receptor isolated from *Staphylococcus aureus*[6].

Indeed, as it originated from the most effective bacterial strain with regard to its ability to combat antibiotics and β-lactames in particular, this receptor used in vitro demonstrated exceptional recognition abilities for all β-lactame compounds, both for penicillins and for cephalosporines (see Ref.[6] and the results shown in the example).

Another advantage of this receptor is to have an alkaline isoelectric point (pI). This offers the opportunity to be able to very easily purify it from a raw extract of cells in order to obtain antibodies from it.

In addition, our choice has also been determined by the observation of a very good immune response in rabbits that is very specific and does not cause any non-specific response with the rest of all the reagents involved in the multi-analyte measurement.

According to the present invention, a method was successfully formulated, in which it is possible to combine in a single operation all the elements required for the common detection of several compounds of different classes by using totally different recognition mechanisms.

The present invention offers the additional advantage of proposing the formulation of a reliable and economical multi-analyte test. Indeed, it is not necessary to purify the receptors nor the antibody preparations and what is more, the receptors are not chemically modified, which should preserve their full reactivity and stability.

Figure 1:
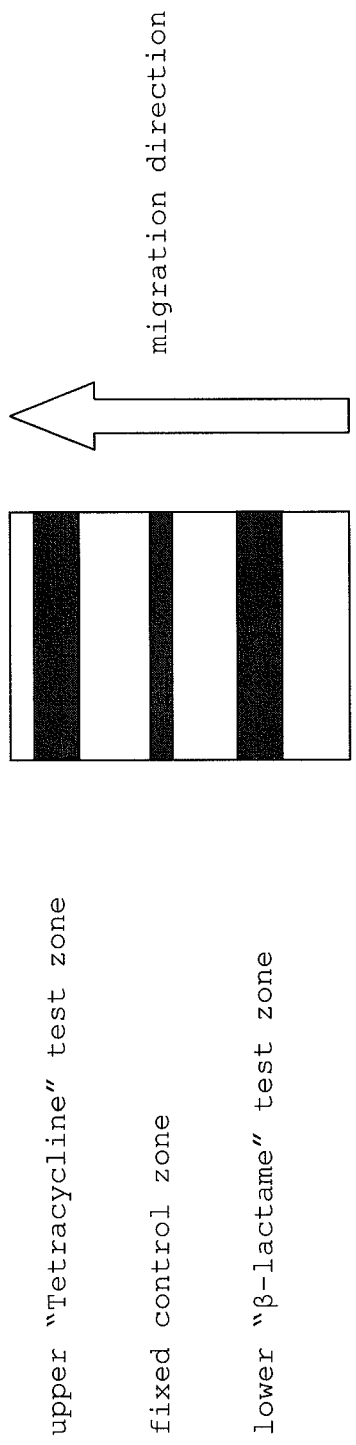
FIG. 1 schematically shows an example of the positioning of the recovery elements according to the invention on a solid nitrocellulose support in the case of the simultaneous measurement of only two antibiotics, a fixed control zone also being provided.

DESCRIPTION OF PREFERRED
EMBODIMENTS OF THE INVENTION

Preliminary Remark

As mentioned in the state of the art, a competition test envisaged according to the present invention may in particular be in two different formats. In the first case (format 1), the receptors are conjugated with particles of colloidal gold and the competitor compounds, analogues of the substance sought, act as recovery elements by being fixed to the specific capture point. In the second case (format 2), the competitor compounds, analogues of the substance sought, are conjugated with the particles of colloidal gold and the receptors act as recovery elements by being fixed to the specific capture point. In certain cases of multi-analyte detection, a mixed system (formats 1 and 2 present) is also possible.

Example No. 1

Simultaneous Measurement of Tetracyclines and β-Lactames by Specific Receptors

Format 1 for Both Detections

The method uses a reactive mixture comprising both respective receptors of β-lactames and tetracyclines as well as their reagents and a recovery element to which specific ligands of these receptors are fixed at precise and distinct points.

Preparation of the Reactive Mixture

For the detection of β-lactames, the reactive mixture comprises the specific receptor for recognising β-lactames, its specific antibody and a preparation of protein A conjugated with colloidal gold. For the detection of tetracyclines, the reactive mixture comprises the receptor of the tetracyclines, its specific antibody, a specific fragment of DNA conjugated with biotin and a preparation of protein A conjugated with colloidal gold.

The β-lactame receptor is obtained by the method described by Golemi-Kotra et al.[6] The unpurified receptor is filtered on a Millex HV membrane (Millipore, Inc., USA) before it is stored at 4° C. in the presence of glycerol at 50% v/v. The tetracycline receptor is obtained by the method described in patent application WO-A-03/048770.

Both antibody preparations are obtained by the method described in Kachab et al.[7] These antibody preparations were obtained by injecting a preparation of purified receptor until protein homogeneity according to Golemi-Kotra et al.[6] for the β-lactame receptor and according to application WO-A-03/048770 for the tetracycline receptor. Both antibody preparations are preferably used unpurified, which means that it is unpurified serum that is directly added to the reactive mixture. According to a second preferred embodiment, the specific antibodies of polyclonal or monoclonal type are purified by methods known to the man skilled in the art and then directly or indirectly bonded to colloidal gold particles according to the Frens method[8].

The DNA fragment is obtained at Eurogentec SA, Belgium according to the sequence and preparation described in patent application WO-A-03/048770. In this precise case, the DNA fragment is not fixed to a capture point on a nitrocellulose membrane but it is directly incorporated into the reactive mixture. This fragment will be recovered in testo by means of its biotinylated end on avidine fixed to a capture point (see below).

All reagents required are introduced without any chemical modification or substitution so as to preserve all the properties of reactivity and stability. These molecules may be purified or unpurified, which has an obvious economical benefit.

In the precise example, the reactive mixture comprises:
  5 parts of β-lactame receptor (RSA) at a concentration of 360 nM;
  5 parts of tetracycline receptor (TetR) at a concentration of 4.2 µM;
  1 part of anti-RSA serum diluted 4× in a buffer of NaPi 50 mM, NaCl 150 mM, pH 7.8;
  1 part of anti-TetR serum diluted 4× in a buffer of NaPi 50 mM, NaCl 150 mM, pH 7.8;
  1 part of nucleic acid at a concentration of 25 µM in NaCl 690 mM;
  15 parts of protein A-gold of 40 nm at an optical density (OD)=10 at 520 nm;
  22 parts of Hepes buffer 120 mM, pH 8, BSA 2%, Dextran 1%, sucrose 5%.

This mixture is either prepared as required or lyophilisated for 20 hours.

The Recovery System

The recovery system comprises a nitrocellulose membrane on which are fixed, at distinct points, the elements capable of forming a complex with the recognition molecules of the reactive mixture. These elements are:
  for the "beta" signal (for β-lactame), an antibiotic, preferably of penicillin or cephalosporine type, fixed to a molecule with no particular reactivity to protein A, biotin or avidine. In a preferred embodiment of the present invention, an ampicillin fixed to a β-lactoglobulin is used;
  for the "tetra" signal (for tetracycline), an avidine capable of recognising a fragment of DNA with a molecule of biotin at one end. An egg-white avidine is preferably used.

The "beta" and "tetra" capture zones may be successively positioned one before the other or vice versa without any particular preference as long as they are arranged at spatially distinct but known locations. It is in fact this distinct position that will allow the type of antibiotic present in the analysis solution to be identified. If both capture systems were positioned at the same point, their measurement would not be affected but it would not be possible to determine which type of compound is actually present.

Preparation of β-Lactoglobulin Conjugated with Ampicillin

β-lactoglobulin is chosen because it is a milk protein that comprises many lysine residues (10%) and the three-dimensional structure indicates that most lysines have their $NH_2$ end facing the outside of the protein (Pubmed, structure, 1GXA).

100 mg of β-lactoglobulin and 15 mg of 2-iminothiolane are incubated in a buffer of NaPi 100 mM, pH 8.5 in a reactive volume of 4 ml for 60 minutes at 25° C. The mixture is then deposited on a PD10 column (Amersham Biosciences, UK) previously equilibrated in PBS pH 7, EDTA 5 mM and eluted in this same buffer. The protein fractions are gathered by well-known methods.

In addition, 2 ml of DMSO comprising 100 mg of SICC are incubated with 2 ml of a solution of 50 mg/ml of sodium ampicillin in a buffer of NaPi 25 mM, pH 8, for 60 minutes at 25° C. before being incubated in the presence of 50 mg of protein solution for 4 hours at 4° C. Lastly, the solution is dialysed twice for 6 hours with 100 volumes of a buffer of NaPi 25 mM, pH 7.5.

Preparation of a Solution of Neutralized Avidine

A solution of 5 mg/ml of egg-white avidine, available at Pierce Inc., USA is prepared in a buffer of NaPi 50 mM, pH 7.5.

Preparation of a Control Solution of BSA-Gold

The present invention recommends the use of a control line of constant intensity and visible before and after the development of the test. This line is preferably of a similar colour to the colour developed in the "test" lines and is synthesized as follows.

To a preparation of 27 ml of colloidal gold of 40 nm, obtained by the Frens[8] method and with an optical density of $OD_{lambda\ max}$ of 3, is added 3 ml of a solution of BSA (Sigma) at 10% in a borate buffer of 10 mM, pH 6.5. The mixture is incubated for 60 minutes at 20° C. before it is centrifuged for 45 minutes at 10,000 rpm in an SS34 rotor (Sorvall). The residue is then recovered in a buffer of NaPi 50 mM, NaCl 150 mM in order to obtain an $OD_{lambda\ max}$ of 45. The solution that will be deposited on the nitrocellulose membrane is further diluted 15 times in that same buffer to obtain a final OD of 3.

Immunochromatographic Technique

The immunochromatographic technique is known and described in the literature (Developing Immunochromatographic Test Strips: A Short Guide, Millipore, Lit. no. TB500 Printed in USA 11/96, 96-204). In the present invention, the preparations obtained above are deposited in precise and distinct positions on a nitrocellulose membrane and preferably successively one behind the other with reference to the migration direction of the liquid. The nitrocellulose membrane is then brought into contact at one end with a membrane, for example, of type 142 available at Ahlstrom, Inc., USA or of type GFDVA available at Whatman, UK but not of type Leukosorb® available at Pall, UK and at the other end by any absorbent paper of for example type 17CHR available at Whatman, UK.

Deposition of the Recovery Elements on the Nitrocellulose Support

It is the positioning of the recovery elements that will allow to identify the type of contamination found in the sample. The solutions are deposited by means of a Biodot (UK) "dispenser" of type Quanti-3000 at a flow rate of 1 µL/cm.

In the case of a detection of two parameters, the preparations of β-lactoglobulin and avidine will be deposited on each side of the control line. For example, the β-lactoglobulin conjugate already prepared will be deposited below the control line and the neutralized avidine solution will be deposited above the control line (FIG. 1). As a result, the presence of β-lactame compounds will be characterized by the absence of marking on the β-lactoglobulin, i.e. on the test line located below the control line, and the presence of tetracycline compounds will be characterized by the absence of marking on the test line above the control line. In the case where both compounds are present in sufficient quantity, neither of the two signals will appear on either side of the control line (see FIG. 1).

Simultaneous Measurement of β-Lactames and Tetracyclines in a Milk Sample

200 µL of cold milk are incubated at 50° C. in the presence of 50 µl of the reagents prepared and/or lyophilisated as above. After 3 minutes of incubation at 50° C., the above-described recovery element is immersed in the solution. The final interpretation is made after 3 minutes of incubation by means of an optical dipstick reader available at Matest (Germany);

The results are set out in Table 1. The method allows to consider as positive a sample of milk with 4 ppb in ampicillin and/or 75 ppb in tetracycline.

Table 2 sets out the detection limits obtained by the present method for the various compounds of the mentioned β-lactames and tetracyclines. As a general rule, when the ratio of the intensities of the concerned test signal relative to the control signal is less than or equal to 1, the sample is considered positive for the parameter (compound) concerned.

TABLE 1

Units and ratios of the intensities measured at the capture points

| Antibiotic concentration (ppb) | Intensity: zone B(*) | Ratio B/C | Intensity: zone T | Ratio T/C | Intensity: Control zone |
|---|---|---|---|---|---|
| Ampi 0 + Tetra 0 | 520 | 2.5 | 410 | 2.0 | 208 |
| Ampi 1 | 380 | 1.9 | 380 | 1.9 | 199 |
| Ampi 2 | 250 | 1.2 | 405 | 1.9 | 211 |

TABLE 1-continued

Units and ratios of the intensities measured at the capture points

| Antibiotic concentration (ppb) | Intensity: zone B(*) | Ratio B/C | Intensity: zone T | Ratio T/C | Intensity: Control zone |
|---|---|---|---|---|---|
| Ampi 3 | 155 | 0.8 | 408 | 2.0 | 205 |
| Ampi 4 | 105 | 0.5 | 386 | 1.9 | 201 |
| Ampi 5 | 55 | 0.3 | 397 | 2.0 | 197 |
| Ampi 10 | 25 | 0.1 | 414 | 2.1 | 200 |
| Ampi 0 + Tetra 25 | 505 | 2.5 | 340 | 1.7 | 206 |
| Ampi 0 + Tetra 50 | 521 | 2.5 | 288 | 1.4 | 206 |
| Ampi 0 + Tetra 75 | 523 | 2.6 | 162 | 0.8 | 203 |
| Ampi 0 + Tetra 100 | 508 | 2.6 | 55 | 0.3 | 199 |
| Ampi 4 + Tetra 75 | 122 | 0.6 | 165 | 0.8 | 202 |

(*)B: beta,
T: tetra,
C: control

TABLE 2

Detection limit

| Antibiotic | MRL/EU (ppb) | Safe level/US (ppb) | Concentration (ppb) | Intensity ratio of parameter/control zone |
|---|---|---|---|---|
| Benzylpenicillin | 4 | 5 | 2 | 0.4 |
| Ampicillin | 4 | 10 | 4 | 0.4 |
| Amoxicillin | 4 | 10 | 4 | 0.4 |
| Cloxacycline | 30 | 10 | 10 | 0.5 |
| Cephapyrin | 60 | 20 | 8 | 0.3 |
| Ceftiofur | 100 | 50 | 10 | 0.5 |
| Tetracycline | 100 | 300 | 75 | 0.8 |
| Oxytetracycline | 100 | 300 | 50 | 0.8 |
| Chlortetracycline | 100 | 300 | 50 | 0.8 |
| Doxycycline | 100 | 300 | 20 | 0.8 |

Example No. 2

Simultaneous Measurement of Tetracyclines, β-Lactames and Sulfamides

Format 1 for the Three Detections

In this preferred embodiment, in addition to both tetracyclines and β-lactames receptors, this method incorporates a specific antibody for the recognition of sulfadimethoxins.

Preparation of the Reactive Mixture

An anti-sulfadimethoxin antibody is moreover added to the above-mentioned mixture according to the following preparation:

5 parts of β-lactame receptor (RSA) at a concentration of 360 nM;
  5 parts of tetracycline receptor (TetR) at a concentration of 4.2 µM;
  1 part of anti-RSA serum diluted 4× in a buffer of NaPi 50 mM, NaCl 150 mM, pH 7.8;
  1 part of anti-TetR serum diluted 4× in this same buffer;
  1 part of anti-sulfadimethoxin diluted 2× in this same buffer;
  1 part of nucleic acid at a concentration of 50 µM;
  20 parts of protein A gold of 40 nm at OD=10 at 520 nm;
  16 parts of Hepes buffer of 120 mM, pH 8, BSA 2%, Dextran 1%, sucrose 5%.

This mixture is prepared either as required or lyophilisated for 20 hours.

The Recovery System

The recovery system is similar to that of example 1, into which a fourth line specific for the recovery of the anti-sulfadimethoxin antibody molecules is incorporated (3$^{rd}$ test line). The other capture zones are identical but differently positioned, as in FIG. 2.

Preparation of a BSA Conjugated with a Sulfadimethoxin

The preparation is achieved by the procedure described by Dixon-Holland and Katz[9]. 100 mg of sulfadimethoxin and 200 mg of BSA solubilized in 25 ml of a mixture, comprising two parts of a phosphate buffer of 50 mM, pH 7.2 and 1 part of dioxane, are incubated in the presence of 120 µL of 25% glutaraldehyde stirred for 3 hours at 25° C. The solution is then dialysed for 6 days at 4° C. against 100 volumes of a buffer of NaPi 50 mM, pH 7.2 with a change of buffer every 12 hours.

Deposition of the Recovery Elements on the Nitrocellulose Support

Figure 2:
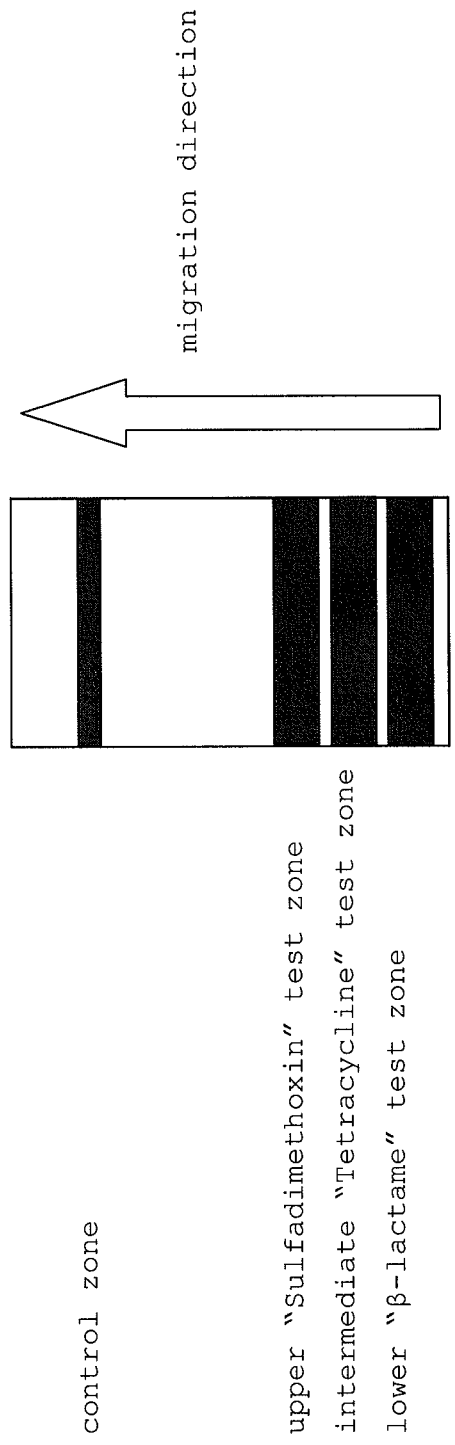
FIG. 2 schematically shows an example of the positioning of the recovery elements according to the invention on a solid nitrocellulose support in the case of the simultaneous measurement of tetracyclines, β-lactames and sulfamides, a fixed control zone also being provided.

In the case of a detection of three parameters, the capture lines are positioned in precise and distinct locations on a nitrocellulose membrane and preferably successively one after the other with reference to the migration direction of the liquid. According to a preferred embodiment, the capture zones for β-lactame, tetracycline and sulfadimethoxin and the control zone are positioned at a first, second, third and finally fourth level, respectively with reference to the migration direction of the liquid (FIG. 2). A single control zone serves as a reference for the three markers. A different formulation, similar to the preceding example, would be to incorporate two control zones, i.e. a control zone between each test zone.

As a general rule, it will be noted that, according to the present invention, the test lines and control lines do not necessarily have to be positioned in the same order relative to the migration direction of the liquid. Thus, the kit works equally well whether the order observed is "beta"-"tetra" or "tetra"-"beta", "beta"-"sulfa" or "sulfa"-"beta" (see example below), "beta"-"tetra"-"sulfa" or "sulfa"-"tetra"-"beta", etc.

Simultaneous Measurement of β-Lactames, Tetracyclines and Sulfadimethoxins in a Sample of Milk 200 µL of cold milk are incubated at 50° C. in the presence of 50 µl of the reagents prepared and/or lyophilisated as above. After 3 minutes of incubation at 50° C., the above-described recovery element is immersed in the solution. The final interpretation is made after 3 minutes of incubation by means of an optical dipstick reader available at Matest (Germany).

The results are set out in Table 3. The method allows to consider as positive a sample of milk with 4 ppb in ampicillin and/or 75 ppb in tetracycline and 100 ppb in sulfadimethoxin.

Table 4 summarizes the detection limits obtained by the method according to the invention for the various β-lactame, tetracycline and sulfadimethoxin compounds mentioned. As a general rule, if the ratio of the intensities of the concerned test signal relative to the control signal is less than or equal to 1, the sample is considered as positive for the parameter (compound) concerned.

TABLE 3

Ratios of measured intensities

| Antibiotic concentration (ppb) | | | Ratio of the measurement intensities | | |
|---|---|---|---|---|---|
| A(*) | T | S | B/C | T/C | S/C |
| 0 | 0 | 0 | 2.5 | 2.0 | 1.9 |
| 1 | 0 | 0 | 1.9 | 1.9 | 1.7 |
| 2 | 0 | 0 | 1.2 | 1.9 | 2.1 |
| 3 | 0 | 0 | 0.8 | 2.0 | 2.2 |
| 4 | 0 | 0 | 0.5 | 1.9 | 2.0 |

TABLE 3-continued

Ratios of measured intensities

| Antibiotic concentration (ppb) | | | Ratio of the measurement intensities | | |
|---|---|---|---|---|---|
| A(*) | T | S | B/C | T/C | S/C |
| 5 | 0 | 0 | 0.3 | 2.0 | 2.0 |
| 10 | 0 | 0 | 0.1 | 2.1 | 1.9 |
| 0 | 25 | 0 | 2.5 | 1.7 | 1.9 |
| 0 | 50 | 0 | 2.5 | 1.4 | 2.2 |
| 0 | 75 | 0 | 2.6 | 0.8 | 2.0 |
| 0 | 100 | 0 | 2.6 | 0.3 | 1.8 |
| 0 | 0 | 50 | 2.4 | 1.9 | 1.3 |
| 0 | 0 | 100 | 2.2 | 1.9 | 0.8 |
| 0 | 0 | 150 | 1.9 | 2.1 | 0.6 |
| 0 | 0 | 200 | 2.4 | 2.1 | 0.4 |
| 4 | 75 | 100 | 0.6 | 0.8 | 0.7 |

(*)A: ampicillin,
T: tetracycline,
S: sulfamide,
C: control

TABLE 4

Detection limit

| Antibiotic | Concentration detection limit (ppb) | Ratio test/control |
|---|---|---|
| Benzylpenicillin | 2 | 0.4 |
| Ampicillin | 4 | 0.4 |
| Amoxicillin | 4 | 0.4 |
| Cloxacycline | 10 | 0.5 |
| Cephapyrin | 8 | 0.3 |
| Ceftiofur | 10 | 0.5 |
| Tetracycline | 75 | 0.8 |
| Oxytetracycline | 50 | 0.9 |
| Chlortetracycline | 50 | 0.7 |
| Doxycycline | 20 | 0.6 |
| Sulfadimethoxin | 100 | 0.8 |

Example No. 3

Simultaneous Measurement of β-Lactames and Sulfamides

Format 1 for β-Lactames and Format 2 for Sulfamides

Preparation of the Reactive Mixture

The reactive mixture comprises:
  5 parts of β-lactame receptor (RSA) at a concentration of 360 nM;
  10 parts of a monoclonal anti-RSA antibody attached to colloidal gold (OD=10 at 520 nm);
  1 part of biotinylated and diluted anti-sulfadimethoxin in NaPi 50 mM, NaCl 150 mM, pH 7.8;
  10 parts of a dilution of BSA-sulfadimethoxin-gold of 40 nm;
  24 parts of Hepes buffer 120 mM, pH 8, BSA 2%, Dextran 1%, sucrose 5%.

This mixture is prepared either as required or lyophilisated for 20 hours.

Biotinylation of the Anti-Sulfadimethoxin Antibody

825 µL of a solution comprising 5 mg/ml of anti-sulfadimethoxin antibody dialysed in a carbonate buffer 100 mM, pH 9.2 are incubated in the presence of 165 µL of a solution of biotin-LC-NHS at 1.5 mg/ml (available at Perbio, Inc.) for 2 hours at 25° C. sheltered from light. The reaction is blocked by the addition of 10 μL of a solution of a Tris buffer 1M pH 8 for 30 minutes before dialysis 2× for 10 hours against a buffer of NaPi 50 mM, NaCl 150 mM, pH 7.8.

Preparation of a BSA-Sulfadimethoxin Conjugated with Gold Particles

The preparation of BSA-sulfadimethoxin described in example no. 2 is used fixed to particles of colloidal gold in a protocol similar to that described in example no. 1 for preparing the control BSA-gold solution.

The Recovery System

The recovery system is identical to that of example 1. However, in the present case, it is the biotinylated antisulfamide antibody that will be recovered in the avidine fixed at the second capture point above the control zone.

Simultaneous Measurement of Lactames and Sulfadimethoxins in a Sample of Milk

200 μL of cold milk are incubated for 15 minutes at 30° C. in the presence of 50 μL of the reagents prepared above. After this first incubation, the above-described recovery element is immersed in the solution. Final interpretation is made after a second incubation of 15 minutes. The results are set out in Table 5.

TABLE 5

Ratios of the measured intensities

| Antibiotic concentration (ppb) | | Ratio of the measurement intensities | |
|---|---|---|---|
| B(*) | S | B/C | S/C |
| 0 | 0 | 2 | 3 |
| 1 | 0 | 1.5 | 2.8 |
| 2 | 0 | 1.2 | 2.9 |
| 3 | 0 | 0.95 | 3 |
| 4 | 0 | 0.8 | 3.1 |
| 5 | 0 | 0.65 | 3.1 |
| 10 | 0 | 0.35 | 2.9 |
| 0 | 0 | 2 | 2.9 |
| 0 | 50 | 1.95 | 2 |
| 0 | 100 | 1.9 | 1 |
| 0 | 150 | 2.2 | 0.85 |
| 0 | 200 | 2.1 | 0.7 |
| 4 | 100 | 0.84 | 0.95 |

(*)B: β-lactame, S: sulfamide, C: control

Example No. 4

Simultaneous Measurement of Tetracyclines and Sulfamides

Format 2 for Both Detections

Preparation of the Reactive Mixture

The reactive mixture comprises:
  5 parts of tetracycline receptor (TetR) at a concentration of 4.2 μM;
  1 part of monoclonal anti-TetR mouse antibody diluted in a buffer of NaPi 50 mM, NaCl 150 mM, pH 7.8;
  1 part of antisulfamide rabbit antibody diluted in this same buffer;
  10 parts of a dilution of BSA-sulfadimethoxin-gold of 40 nm;
  1 part of biotinylated nucleic acid at a concentration of 50 μM;
  10 parts of an anti-biotin-gold antibody of 40 nm at OD=10 at 520 nm;
  22 parts of Hepes buffer 120 mM, pH 8, BSA 2%, Dextran 1%, sucrose 5%.

This mixture is either prepared as required or lyophilisated for 20 hours.

The Recovery System

The recovery system is similar to that of example 1. However, in the present case, it is an anti-mouse antibody that forms the first capture point where the monoclonal anti-TetR antibody will be recovered and it is a chicken anti-rabbit antibody that forms the second capture point where the antisulfamide antibody will be recovered.

Simultaneous Measurement of Tetracyclines and Sulfamides in a Sample of Meat 30 ml of a buffer of NaPi 50 mM, pH 8 is added to 10 g of pig muscle and the mixture is mixed with a mixer of type MiniMix (Interscience, F) for 2 minutes. The solution, collected in an Eppendorf tube, is then centrifuged for 1 minute at 6,000 rpm to recover the supernatant from it. 200 μL of supernatant are incubated for 15 minutes at 25° C. in the presence of 50 μL of the reagents prepared above. After this first incubation, the above-described recovery element is immersed in the solution. The final interpretation is made after a second incubation of 15 minutes. The results are set out in Table 6.

TABLE 6

Ratios of the measured intensities

| Antibiotic concentration (ppb) | | Ratio of the measurement intensities | |
|---|---|---|---|
| T(*) | S | T/C | S/C |
| 0 | 0 | 3.2 | 2.1 |
| 25 | 0 | 2.5 | 2.2 |
| 50 | 0 | 1.6 | 2.2 |
| 75 | 0 | 1.1 | 2.1 |
| 100 | 0 | 0.5 | 2 |
| 200 | 0 | 0 | 1.9 |
| 0 | 0 | 3.2 | 2.2 |
| 0 | 50 | 3.4 | 1.6 |
| 0 | 100 | 3.1 | 1 |
| 0 | 150 | 3.4 | 0.85 |
| 0 | 200 | 3 | 0.7 |
| 100 | 100 | 0.4 | 0.95 |

(*)T: tetracycline, S: sulfamide, C: control

Example 5

Simultaneous Measurement of β-Lactames, Tetracyclines and Sulfamides

Format 1 for β-Lactames/Tetracyclines and Format 2 for Sulfamides

Preparation of the Reactive Mixture

The reactive mixture comprises:
  5 parts of β-lactame receptor (RSA) at a concentration of 360 nM;
  1 part of monoclonal anti-RSA mouse antibody diluted in a buffer of NaPi 50 mM, NaCl 150 mM, pH 7.8;
  5 parts of tetracycline receptor (TetR) at a concentration of 4.2 μM;
  1 part of monoclonal anti-TetR mouse antibody diluted in a buffer of NaPi 50 mM, NaCl 150 mM, pH 7.8;
  1 part of biotinylated nucleic acid at a concentration of 50 μM;
  1 part of polyclonal antisulfamide rabbit antibody diluted in a buffer of NaPi 50 mM, NaCl 150 mM, pH 7.8;

7 parts of a dilution of BSA-sulfadimethoxin-gold of 40 nm;

13 parts of an anti-mouse antibody attached to colloidal gold of 40 nm at OD=10 at 520 nm;

16 parts of Hepes buffer 120 mM, pH 8, BSA 2%, Dextran 1%, sucrose 5%.

This mixture is either prepared as required or lyophilisated for 20 hours.

In a second preferred method, both monoclonal anti-RSA and anti-TetR antibodies are directly conjugated with particles of colloidal gold.

The Recovery System

The recovery system is similar to that of example 1. However, in the present case, it is lactoglobulin-ampicillin that forms the first capture point where the RSA receptor will be recovered, it is avidine at the second capture point where the TetR receptor will be recovered and it is an anti-rabbit chicken antibody that forms the third capture point where the antisulfamide rabbit antibody will be recovered.

Simultaneous Measurement of β-Lactames, Tetracyclines and Sulfamides in a Sample of Milk 200 µL of cold milk are incubated for 15 minutes at 30° C. in the presence of 50 µL of the reagents prepared above. After this first incubation, the above-described recovery element is immersed in the solution. Final interpretation is made after a second incubation of 15 minutes. The results are set down in Table 7.

TABLE 7

Ratios of measured intensities

| Antibiotic concentration (ppb) | | | Ratio of the measurement intensities | | |
|---|---|---|---|---|---|
| B(*) | T | S | B/C | T/C | S/C |
| 0 | 0 | 0 | 2 | 3 | 1.8 |
| 2 | 0 | 0 | 1.3 | 2.7 | 1.8 |
| 4 | 0 | 0 | 0.9 | 2.7 | 1.7 |
| 10 | 0 | 0 | 0.5 | 2.8 | 1.9 |
| 0 | 50 | 0 | 1.9 | 1.4 | 1.9 |
| 0 | 100 | 0 | 2 | 0.6 | 2 |
| 0 | 0 | 50 | 2.1 | 2.8 | 1.3 |
| 0 | 0 | 100 | 1.8 | 2.7 | 0.9 |
| 0 | 0 | 200 | 1.8 | 3 | 0.3 |
| 4 | 100 | 100 | 0.95 | 0.7 | 0.8 |

(*)B: β-lactame,
T: tetracycline,
S: sulfamide,
C: control

REFERENCES

[1] Council Directive 96/23/CE dated Apr. 29, 1996, on measures to monitor certain substances and residues thereof in live animals and animal products and abrogating Directives 85/358/CEE and 86/469/CEE and Decisions 89/187/CEE et 91/664/CEE.

[2] Council Regulation (EEC) No 2377/90 dated Jun. 26, 1990 laying down a Community procedure for the establishment of maximum residue limits for veterinary medicinal products in foodstuffs of animal origin.

[3] Off. J. Eur. Comm. 2002, L221/8-2002/657/CE.

[4] Hisao Oka, *Chemical Analysis for Antibiotics Used in Agriculture*, by AOAC INTERNATIONAL, 1995, ISBN 0-935584-57-9.

[5] Ron Verheijen et al, Analyst 123 (1998), 2437-2441.

[6] Golemi-Kotra, D. et al, The Journal of Biological Chemistry, Vol. 278, n° 20 (May 2003), pp. 18419-18425.

[7] Kachab, E. H. et al, The Journal of Immunology Methods, Vol 147, n° 1 (1992), pp. 33-41.

[8] Frens, G., Nature (London), Phys. Sci., 241 (1973), 20.

[9] Dixon-Holland, D. E. et Katz, S. E., (1988), J. Assoc. Off. Anal. Chem. (1988) 71 (6), 1137-40.

The invention claimed is:

1. Diagnostic kit for the simultaneous measurement of antibiotics of different classes, at least β-lactames and tetracyclines, comprising:

a single reactive mixture comprising at least a first labeled receptor specific for the recognition of β-lactames, a second labeled receptor and a biotinylated fragment of a nucleic acid, so that the second labeled receptor specifically and competitively recognizes a tetracycline present in a sample and said biotinylated fragment of a nucleic acid;

and a recovery system in the form of a solid support comprising a single nitrocellulose membrane on which are attached at two known and distinct sections, called test zones, an antibiotic with a β-lactame core and an avidine, respectively;

in such a way that the labeling intensity detected on the recovery system in both test zones independently results from the competitive recognition of each antibiotic by its labeled receptor.

2. The diagnostic kit according to claim 1, wherein the antibiotic with a β-lactame core and the avidine bound to the nitrocellulose membrane are a penicillin or a cephalosporine and an egg white avidine respectively.

3. The diagnostic kit of claim 2, wherein said penicillin is an ampicillin fixed to a β-lactoglobulin.

4. The diagnostic kit according to claim 1, wherein the single nitrocellulose membrane is deposited on a dipstick support on which it is in contact at a first end with an entry membrane and at a second end with an absorbent paper, has two distinct said test zones on which are attached the antibiotic with a β-lactame core and the avidine, respectively, one after the other in the migration direction of a liquid, and has a control zone.

5. The diagnostic kit of claim 4, wherein the control zone is located between the two test zones.

6. The diagnostic kit according to claim 4, wherein the control zone is obtained by means of any protein preparation labeled by particles of colloidal gold.

7. The diagnostic kit of claim 6, wherein said protein preparation is labeled by means of a bovine serumalbumin or BSA attached to the particles of colloidal gold.

8. The diagnostic kit for the simultaneous measurement of β-lactames, tetracyclines and sulfamides according to claim 1, wherein the reactive mixture also comprises a labeled antibody specific for the recognition of sulfamides, and the recovery system also comprises a preparation of protein conjugated with a sulfamide, fixed to the nitrocellulose membrane.

9. The diagnostic kit for the simultaneous measurement of β-lactames, tetracyclines and sulfamides according to claim 8, wherein the nitrocellulose membrane is deposited on a dipstick support on which it is in contact at a first end with an entry membrane and at a second end with an absorbent paper, has three distinct said test zones on which are attached the antibiotic with a β-lactame core, the avidine and the protein conjugated with a sulfamide, respectively, and has a control zone, successively arranged one after the other in the migration direction of a liquid, or two control zones, each alternately arranged between two of said three test zones.

10. The diagnostic kit of claim 8, wherein said labeled antibody specific for the recognition of sulfamides is labeled, directly or indirectly by particles of colloidal gold.

11. The diagnostic kit according to claim 1, wherein the second labeled receptor is able to recognize the tetracycline in the sample, wherein the sample is essentially liquid and is obtained from milk, honey, meat, eggs or biological liquids.

12. The diagnostic kit according to claim 1, wherein the labeled receptors specific for the recognition of the β-lactames and tetracyclines are the receptors BlaR and TetR respectively isolated from known classes of micro-organisms.

13. The diagnostic kit of claim 12, wherein receptor BlaR is isolated from *Staphylococcus aureus* and TetR is isolated from plasmid pSC101 of *E. Coli* 600.

14. The diagnostic kit of claim 1, wherein both labeled receptors are labeled by labeling particles, either directly or indirectly by means of a specific anti-receptor antibody, alone or in association with protein A, added to the reactive mixture.

15. The diagnostic kit of claim 14, wherein said labeling particles are particles of colloidal gold.

16. The diagnostic kit according to claim 14, wherein the specific anti-receptor antibody added to the reactive mixture is a monoclonal or polyclonal antibody, modified or unmodified chemically or by recombination, purified or unpurified, attached or unattached, directly or indirectly to the labeling particles.

17. The diagnostic kit for the simultaneous measurement of β-lactames, tetracyclines and sulfamides according to claim 1, wherein the reactive mixture also comprises an antisulfamide antibody and a labeled analogue of a sulfamide, and the recovery system also comprises an antibody targeting said antisulfamide antibody, fixed to the nitrocellulose membrane.

18. A method for the simultaneous measurement of antibiotics of different classes, comprising:
  (1) bringing a single reactive mixture into contact with a sample to be classified, wherein said reactive mixture comprises at least a first labeled receptor specific for the recognition of β-lactames, a second labeled receptor and a biotinylated fragment of a nucleic acid, so that the second labeled receptor specifically and competitively recognises a tetracycline and said biotinylated fragment of a nucleic acid, and an antisulfamide antibody and a labeled analogue of a sulfamide;
  (2) incubating the solution obtained in step (1) at a temperature between 30° C. and 50° C. for 3 to 15 minutes;
  (3) immersing a dipstick bearing a recovery system in the solution obtained in step (2) and incubating for 3 to 15 minutes, wherein said recovery system is in the form of a solid support comprising a single nitrocellulose membrane to which are attached at three known and distinct positions, called test zones, an antibiotic with a β-lactame core, an avidine and an antibody targeting the antisulfamide antibody, respectively, and
  (4) interpreting the result on the dipstick either visually by the naked eye or by means of an optical dipstick reader.

19. The method of claim 18, wherein both receptors are labeled by colloidal gold particles, either directly or indirectly by means of an antibody or an antibody in association with protein A.

* * * * *

UNITED STATES PATENT AND TRADEMARK OFFICE
CERTIFICATE OF CORRECTION

| | | |
|---|---|---|
| PATENT NO. | : 7,998,754 B2 | Page 1 of 1 |
| APPLICATION NO. | : 11/911375 | |
| DATED | : August 16, 2011 | |
| INVENTOR(S) | : Granier | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 584 days.

Signed and Sealed this

Twenty-fourth Day of January, 2012

David J. Kappos
*Director of the United States Patent and Trademark Office*